United States Patent

Loev et al.

[11] Patent Number: 4,472,584
[45] Date of Patent: Sep. 18, 1984

[54] N-SUBSTITUTED-1-AMINOALKYL-1,4-DIHYDROPYRIDINES

[75] Inventors: Bernard Loev, Scarsdale; Howard Jones, Ossining, both of N.Y.; John T. Suh, Greenwich, Conn.

[73] Assignee: USV Pharmaceutical Corporation, Tarrytown, N.Y.

[21] Appl. No.: 471,959

[22] Filed: Mar. 3, 1983

[51] Int. Cl.³ .................. C07D 211/82; C07D 401/04; C07D 405/04; A61K 31/455
[52] U.S. Cl. .................... 546/321; 546/167; 546/257; 546/258; 546/269; 546/270; 546/274; 546/280; 546/281; 546/283; 546/284; 544/333; 424/266
[58] Field of Search .............. 546/321, 284, 283, 257, 546/280, 281, 269, 167, 139, 274; 544/333, 238, 405; 424/266, 250, 251, 258

[56] References Cited
FOREIGN PATENT DOCUMENTS
51-70767  6/1976  Japan.

Primary Examiner—Henry R. Jiles
Assistant Examiner—Dale A. Bjorkman

[57] ABSTRACT

Compounds of the formula:

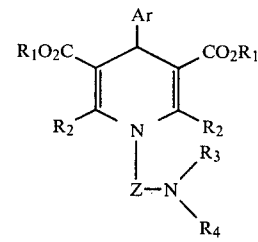

wherein Ar is heteroaryl, cycloalkyl having from 3 to 7 carbon atoms, naphthyl, indanyl, indenyl, tetrahydro naphthyl, or a radical of the formula

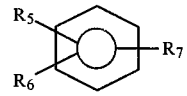

wherein each of $R_5$, $R_6$ and $R_7$ is independently H, alkyl, aryl, halo, lower alkoxy, nitro, amino, alkylmercapto, cyano, carboxy, carbalkoxy, sulfamyl, trifluoromethyl, hydroxy, acyloxy, methanesulfonyl, alkylamino or acylamino; and $R_5$ and $R_6$ when taken together, form a methylenedioxy; Z is alkylene containing 1 to about 5 carbon atoms in the principal chain; each $R_1$ is independently hydrogen, alkyl or alkoxyalkyl, with the proviso that only one $R_1$ may be hydrogen; $R_2$ is lower alkyl; $R_3$ is hydroxyalkyl containing 2 to 4 carbon atoms and $R_4$ is H, alkyl, cycloalkyl or hydroxyalkyl containing 2 to 4 carbon atoms; wherein the alkyl, alkoxy, and acyl groups contain up to 10 carbon atoms, and their pharmaceutically-acceptable salts are disclosed. These compounds have anti-hypertensive activity.

16 Claims, No Drawings

N-SUBSTITUTED-1-AMINOALKYL-1,4-DIHYDROPYRIDINES

This invention relates to new anti-hypertensive agents and more particularly to certain new substituted 1,4-dihydropyridines possessing useful anti-hypertensive activity.

Substituted 1,4-dihydropyridines are known and have been described in the literature as vasodilating agents. 1,4-Dihydropyridines having vasodilating activity are characterized by the presence of alkyl substituents in the 2 and 6 positions of the pyridine ring and carbalkoxy groups in the 3,5-positions usually with a substituent, most commonly phenyl or substituted phenyl, in the 4-position. To increase the water-solubility of these compounds, M. Iwanami, et al. [Chem. Pharm. Bull. 27 (6), 1426–1440 (1979)] described the effect of N-substitution of the pyridine ring nitrogen with, inter alia, aminoalkylene groups such as pyrrolidinoethyl and dimethylaminoethyl. Thus, water-solubility determinations with compounds such as diethyl 1,4-dihydro-4-(3-nitrophenyl)-2,6-dimethyl-1-(2-pyrrolidinoethyl)-3,5-pyridinedicarboxylate and the corresponding 1-(2-dimethylaminoethyl) compound were determined as was the potency thereof as vasodilators but these compounds were determined to be of lower potency than known compounds such as the corresponding 1-ethoxymethyl compound.

Japanese specification No. 70767/76 describes an anti-hypertensive and vasodilating agents 1,4-dihydropyridines of the formula

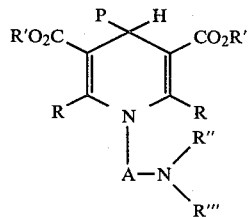

in which R is alkyl; P is substituted (mono or di-) phenyl, pyridyl, furyl, or thienyl in which the substituents are H, halogen, —CN, —NO₂, —NH₂, —N(CH₃)₂, carboxyl, methoxy, ethoxy, butoxy, sulfonyl, methylsulfonyl or acetyl; R' is alkyl, aralkyl, methyl, ethyl, isopropyl, t-butyl, ethoxyethyl, benzyl, phenethyl, or 4-methoxybenzyl; A is alkylene; and R'' and R''' are each alkyl and, when taken together, form a pyrrolidine ring with the N to which they are attached.

The new compounds of the present invention are N-hydroxyalkyl dihydropyridines of the formula

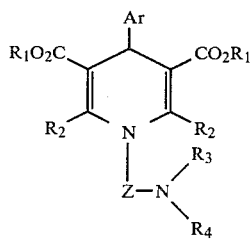

FORMULA I wherein Ar is heteroaryl, cycloalkyl having from 3 to 7 carbon atoms, naphthyl, indanyl, indenyl, tetrahydronaphthyl, or a radical of the formula

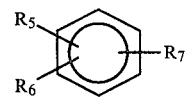

wherein each of $R_5$, $R_6$ and $R_7$ is independently H, alkyl, aryl, halo, lower alkoxy, nitro, amino, alkylmercapto, cyano, carboxy, carbalkoxy, sulfamyl, trifluoromethyl, hydroxy, acyloxy, methanesulfonyl, alkylamino or acylamino; and $R_5$ and $R_6$ when taken together, form a methylenedioxy; Z is alkylene containing 1 to about 5 carbon atoms in the principal chain; each $R_1$ is independently hydrogen, alkyl or alkoxyalkyl, with the proviso that only one $R_1$ may be hydrogen; $R_2$ is lower alkyl; $R_3$ is hydroxyalkyl containing 2 to 4 carbon atoms and $R_4$ is H, alkyl, cycloalkyl or hydroxyalkyl containing 2 to 4 carbon atoms; wherein the alkyl, alkoxy, and acyl groups contain up to 10 carbon atoms, and pharmaceutically-acceptable salts thereof. The total number of carbon atoms in each such hydrocarbyl substituent can range up to about 10. The substituent "Z" contains up to about 5 carbons in the principal chain, i.e. the straight chain of carbons between the terminal valences, but can be branched in that methyl and ethyl substituents can be present on the principal chain. Thus, the alkylene chain Z can contain a total number of carbon atoms greater than 5, preferably no more than about 8.

Heteroaryl as employed herein refers to any heterocyclic structure in which at least one of O, S and N are present as the hetero atoms. These include thiophene, furan, pyridine, thiazole, pyrimidine, pyrrole, benzofuran, quinoline, benzothiophene and substituted heterocycles.

The preferred compounds are those in which the hydrocarbyl radicals contain up to about 7 carbon atoms when aliphatic and up to about 10 carbon atoms when aromatic, e.g., phenyl, tolyl and naphthyl.

The particularly preferred compounds of the invention are those in which Z is —CH₂CH₂— and Ar is a nitrophenyl or trifluoromethylphenyl group, especially 2-trifluoromethylphenyl or 2-nitrophenyl.

The new compounds of the invention can be prepared by art-recognized procedures from known starting compounds as described, for example, in the literature hereinbefore described. The following procedure constitutes a particularly convenient preparative method:

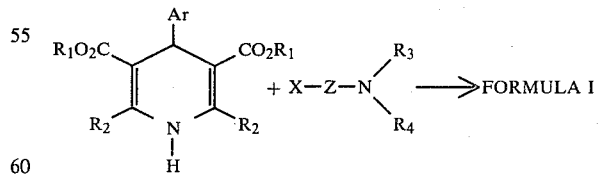

The reaction can be carried out in a solvent in the presence of sodium hydride, or any alkali metal hydride or alkoxide as is commonly employed in condensation reactions. The reaction is effected in two stages, the first, metallation with the alkali metal compound, and the second, condensation with the halide, "X", containing compound, which is usually chloride. The hydrides are convenient since the progress of the metallation reaction can be followed by observing the evolution of hydrogen gas. The metallation step is normally carried out at room temperature. The reaction mixture thereafter is heated at elevated temperature, e.g. at steam bath temperature at or about 100° C., or above up to about 150° C. depending on the boiling point of the selected solvent, and the halide compound is then added, usually in controlled amounts in dropwise fashion and, after addition is completed, the reaction mixture is digested by heating at the elevated temperature.

The product is then obtained in the usual fashion, as by cooling to cause precipitation or evaporation of the solvent followed by removal of protecting group via hydrogenation or simple cleavage reaction to obtain the product as residue.

Employing this procedure, a variety of new N-hydroxyalkyl 1,4-dihydropyridines of the following formula can be prepared:

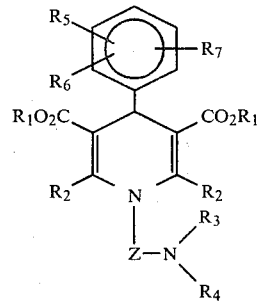

FORMULA II

| Z | $R_2$ | $R_1$ | $R_3$ | $R_4$ | $R_7$ at 4 position | $R_6$ at 3 position | $R_5$ at 2 position |
|---|---|---|---|---|---|---|---|
| CHCH$_3$ | CH$_3$ | C$_2$H$_5$ | CH$_2$CH$_2$OH | CH$_3$ | H | H | H |
| CHCH$_3$ | CH$_3$ | C$_2$H$_5$ | CH$_2$CH$_2$OH | CH$_3$ | H | CH$_3$ | H |
| CH$_2$CH$_2$ | CH$_3$ | C$_2$H$_5$ | CH$_2$CH$_2$OH | H | H | H | H |
| CH(CH$_3$)CH$_2$ | C$_2$H$_5$ | C$_2$H$_5$ | CH$_2$OH | H | H | H | Cl |
| CH$_2$CH$_2$ | CH$_3$ | i-C$_3$H$_7$ | CH$_2$CH$_2$OH | CH$_2$CH$_2$OH | H | CN | H |
| CH$_2$CH$_2$ | CH$_3$ | C$_2$H$_5$ | CH$_2$CH$_2$OH | CH$_3$ | H | H | NO$_2$ |
| CH$_2$CH$_2$ | CH$_3$ | C$_2$H$_5$ | CH$_2$CH$_2$OH | H | H | OH | H |
| CH$_2$CH$_2$ | C$_3$H$_7$ | CH$_3$ | CH$_2$CH$_2$OH | CH$_3$ | H | H | CF$_3$ |
| CH(CH$_3$) | C$_4$H$_9$ | C$_2$H$_5$ | CH$_2$CH$_2$OH | CH$_3$ | H | OCH$_3$ | H |
| (CH$_2$)$_3$ | C$_6$H$_{13}$ | C$_2$H$_5$ | CH$_2$CH$_2$OH | C$_6$H$_{11}$ | H | COOH | H |
| CH$_2$CH$_2$ | i-C$_4$H$_9$ | CH$_3$ | CH$_2$CH(CH$_3$)OH | C$_6$H$_{11}$ | OCH$_3$ | H | H |
| CH$_2$CH$_2$ | CH$_3$ | C$_2$H$_5$ | CH$_2$CH(CH$_3$)OH | C$_6$H$_{11}$ | H | OCH$_3$ | OCH$_3$ |
| (CH$_2$)$_5$ | CH$_3$ | C$_2$H$_5$ | CH$_2$CH$_2$OH | CH$_3$ | H | CH$_3$ | CH$_3$ |
| CH$_2$CH$_2$ | CH$_3$ | C$_2$H$_5$ | CH$_2$CH$_2$OH | CH$_3$ | H | H | CH$_2$C$_6$H$_5$ |
| CH$_2$CH$_2$ | CH$_3$ | C$_2$H$_5$ | (CH$_2$)$_4$OH | C$_6$H$_{11}$ | H | H | C(CH$_3$)$_3$ |
| CH(CH$_3$)CH$_2$ | CH$_3$ | C$_2$H$_5$ | CH$_2$CH$_2$OH | CH$_2$CH$_2$OH | H | H | C$_6$H$_5$ |
| CH$_2$CH$_2$ | CH$_3$ | C$_2$H$_5$ | CH$_2$CH$_2$OH | C$_6$H$_{11}$ | H | H | H |
| CH$_2$CH$_2$ | C$_2$H$_5$ | CH$_3$ | CH$_2$CH$_2$OH | CH$_3$ | H | H | CF$_3$ |
| CH$_2$CH$_2$ | C$_2$H$_5$ | CH$_3$ | CH$_2$CH$_2$OH | CH$_3$ | H | H | NO$_2$ |
| CH$_2$CH$_2$ | C$_2$H$_5$ | CH$_3$ | CH$_2$CH$_2$OH | C$_6$H$_{11}$ | H | H | NO$_2$ |
| CH$_2$CH$_2$ | C$_2$H$_5$ | CH$_3$ | CH$_2$CH$_2$OH | C$_6$H$_{11}$ | H | H | CF$_3$ |
| CH$_2$CH$_2$ | C$_2$H$_5$ | CH$_3$ | CH$_2$CH$_2$OH | H | H | H | CF$_3$ |
| CH$_2$CH$_2$ | C$_2$H$_5$ | CH$_3$ | CH$_2$CH$_2$OH | H | H | H | NO$_2$ |
| CH$_2$CH$_2$ | C$_2$H$_5$ | CH$_3$ | CH$_2$CH$_2$OH | CH$_2$CH$_2$OH | H | H | NO$_2$ |
| CH$_2$CH$_2$ | C$_2$H$_5$ | CH$_3$ | CH$_2$CH$_2$OH | CH$_2$CH$_2$OH | H | H | CF$_3$ |
| CH$_2$CH$_2$ | CH$_3$ | C$_2$H$_5$ | CH$_2$CH$_2$OH | CH$_3$ | Cl | Cl | Cl |
| CH$_2$CH$_2$ | CH$_3$ | C$_2$H$_5$ | CH$_2$CH$_2$OH | CH$_3$ | Cl | H | Cl |
| CH$_2$CH$_2$ | CH$_3$ | C$_2$H$_5$ | CH$_2$CH(CH$_3$)OH | C$_6$H$_{11}$ | Cl | H | Cl |
| CH$_2$CH$_2$ | CH$_3$ | C$_2$H$_5$ | (CH$_2$)$_4$OH | C$_6$H$_{11}$ | OCH$_3$ | H | CH$_2$=CH—CH$_2$ |
| CH$_2$CH$_2$ | CH$_3$ | C$_2$H$_5$ | CH$_2$CH$_2$OH | C$_6$H$_{11}$ | H | H | H |
| CH$_2$CH$_2$ | CH$_3$ | C$_2$H$_5$ | CH$_2$CH$_2$OH | CH$_2$CH$_2$OH | H | CH$_3$ | H |
| CH$_2$CH$_2$ | CH$_3$ | C$_2$H$_5$ | CH$_2$CH$_2$OH | CH$_2$CH$_2$OH | H | H | H |
| CH$_2$CH$_2$ | CH$_3$ | C$_2$H$_5$ | CH$_2$CH$_2$OH | C$_6$H$_{11}$ | H | H | H |
| CH$_2$CH$_2$ | CH$_3$ | C$_2$H$_5$ | CH$_2$CH$_2$OH | C$_6$H$_{11}$ | H | CH$_3$ | H |
| CH$_2$CH$_2$ | CH$_3$ | C$_2$H$_5$ | CH$_2$OH | CH$_2$CH$_2$OH | H | CH$_3$ | CH$_3$ |
| CH$_2$CH$_2$ | CH$_3$ | C$_2$H$_5$ | CH$_2$CH$_2$OH | CH$_3$ | H | H | Cl |
| CH$_2$CH$_2$ | CH$_3$ | C$_2$H$_5$ | CH$_2$CH$_2$OH | CH$_3$ | H | CN | H |
| CH$_2$CH$_2$ | CH$_3$ | C$_2$H$_5$ | CH$_2$CH$_2$OH | CH$_3$ | NO$_2$ | H | H |
| CH$_2$CH$_2$ | CH$_3$ | C$_2$H$_5$ | CH$_2$CH$_2$OH | C$_6$H$_{11}$ | H | OH | H |
| CH$_2$CH$_2$ | CH$_3$ | C$_2$H$_5$ | CH$_2$CH(CH$_3$)OH | C$_6$H$_{11}$ | H | CF$_3$ | H |
| CH$_2$CH$_2$ | CH$_3$ | C$_2$H$_5$ | CH$_2$CH$_2$OH | H | H | OCH$_3$ | H |
| CH$_2$CH$_2$ | CH$_3$ | C$_2$H$_5$ | CH$_2$CH$_2$OH | C$_6$H$_{11}$ | H | COOH | H |
| CH$_2$CH$_2$ | CH$_3$ | C$_2$H$_5$ | CH$_2$CH$_2$OH | H | OCH$_3$ | H | H |
| CH$_2$CH$_2$ | CH$_3$ | C$_2$H$_5$ | CH$_2$CH$_2$OH | CH$_2$CH$_2$OH | H | OCH$_3$ | OCH$_3$ |
| CH$_2$CH$_2$ | CH$_3$ | C$_2$H$_5$ | CH$_2$CH$_2$OH | H | H | H | OCH$_3$ |
| CH$_2$CH$_2$ | CH$_3$ | C$_2$H$_5$ | CH$_2$CH$_2$OH | C$_6$H$_{11}$ | OCH$_3$ | H | CH$_2$=CH—CH$_2$— |
| CH$_2$CH$_2$ | CH$_3$ | C$_2$H$_5$ | CH$_2$CH$_2$OH | CH$_2$CH$_2$OH | H | H | COOCH$_3$ |
| CH$_2$CH$_2$ | CH$_3$ | C$_2$H$_5$ | CH$_2$CH$_2$OH | C$_6$H$_{11}$ | OCH$_3$ | H | COOCH$_3$ |
| CH$_2$CH$_2$ | CH$_3$ | C$_2$H$_5$ | CH$_2$CH$_2$OH | C$_6$H$_{11}$ | H | H | —(CH$_2$)$_4$— |

FORMULA II

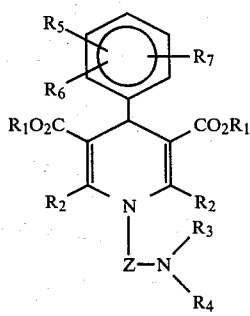

| Z | $R_2$ | $R_1$ | $R_3$ | $R_4$ | $R_7$ at 4 position | $R_6$ at 3 position | $R_5$ at 2 position |
|---|---|---|---|---|---|---|---|
| $CH_2CH_2$ | $CH_3$ | $C_2H_5$ | $CH_2CH_2OH$ | $C_6H_{11}$ | H | H | $NH_2$ |

The present new heterocyclic compounds are therapeutically useful as such or can be employed in the form of salts in view of their basic nature. Thus, these compounds form salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present new compounds. Therefore, all acid salts of the present new compounds are contemplated by the present invention.

The pharmaceutically-acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycolic, gluconic, succinic, arylsulfonic, e.g. p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

As therapeutic agents, the present new heterocyclic compounds are particularly useful in anti-hypertensive agents. The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other antihypertensive agents and the dosage level is of the same order of magnitude as is generally with these other therapeutic agents. The therapeutic dosage will generally be from 10 to 750 milligrams per day and higher, although it may be administered in several different dosage units. Tablets containing from 10 to 250 mg. of active agent are particularly useful.

The following examples further illustrate the invention.

EXAMPLE I

Diethyl 1,4-dihydro-4-(2-trifluoromethylphenyl)-2,6-dimethyl-1-[2-(N-methyl-N-hydroxyethyl)aminoethyl]-3,5-pyridine dicarboxylate To a suspension of sodium hydride (5.2 gms.; 0.11 mole) (50% suspension in mineral oil) in 100 ml of dry distilled DMF is added a solution of diethyl 1,4-dihydro-4-(2-trifluoromethylphenyl)-2,6-dimethyl-3,5-pyridine dicarboxylate (39.7 gms.; 0.1 mole) in 150 ml of DMF. After the gassing has ceased the reaction mixture is heated on a water bath for 1 hour and then is cooled to 50° C. and to the hot solution is added quickly a toluene solution of 2-chloro-[N-methyl-N-benzyloxyethyl]ethylamine. The reaction mixture is heated at 100°–110° C. for a period of 8 hours and then cooled. The unreacted NaH and NaCl is filtered off and the solvent removed from the filtrate. The residue is extracted with hot hexane which, on cooling, affords the product. Recrystallization from hexane followed by debenzylation using hydrogen and palladium on carbon yields the pure desired product.

EXAMPLE II

Diethyl 1,4-dihydro-4-(2-trifluoromethylphenyl)-2,6-dimethyl-1-[2-(N-hydroxyethyl-N-cyclohexyl)aminoethyl]-3,5-pyridine dicarboxylate To a suspension of sodium hydride (5.2 gms.; 0.11 mole) (50% suspension in mineral oil) in 100 ml of dry distilled DMF is added a solution of diethyl 1,4-dihydro-4-(2-trifluoromethylphenyl)-2,6-dimethyl-3,5-pyridine dicarboxylate (39.7 gms.; 0.1 mole) in 150 ml of DMF. After the gassing has ceased the reaction mixture is heated on a water bath for 1 hour and then is cooled to 50° C. and to the hot solution is added quickly a toluene solution of 2-chloro-[N-benzyloxyethyl-N-cyclohexyl]ethylamine. The reaction mixture is heated at 100°–110° C. for a period of 8 hours and then cooled. The unreacted NaH and NaCl is filtered off and the solvent removed from the filtrate. The residue is extracted with hot hexane which, on cooling affords the product. Recrystallization from hexane followed by debenzylation using hydrogen and palladium on carbon yields the pure desired product.

EXAMPLE III

Diethyl 1,4-dihydro-4-(2-trifluoromethylphenyl)-2,6-dimethyl-1-[2-(N-hydroxyethyl)aminoethyl]-3,5-pyridine dicarboxylate To a solution of sodium hydride (5.2 gms.; 0.11 mole) (50% suspension in mineral oil) in 100 ml of dry distilled DMF is added a solution of diethyl 1,4-dihydro-4-(2-trifluoromethylphenyl)-2,6-dimethyl-3,5-pyridine dicarboxylate (39.7 gms.; 0.1 mole) in 150 ml of DMF. After the gassing has ceased the reaction mixture is heated on a water bath for 1 hour and then is cooled to 50° C. and to the hot solution is added quickly a toluene solution of 2-chloro-N-benzyl-N-benzyloxyethyl-ethylamine. The reaction mixture is heated to 100°–110° C. for a period of 8 hours and then cooled. The unreacted NaH and NaCl is filtered off and then solvent removed from the filtrate. The residue is extracted with hot hexane which, on cooling, affords the product. Recrystallization from hexane followed by debenzylation using palladium on carbon yields pure desired product.

EXAMPLE IV

Diethyl 1,4-dihydro-4-(2-trifluoromethylphenyl)-2,6-dimethyl-1-[2-(N,N-dihydroxyethyl)aminoethyl]-3,5-pyridine dicarboxylate To a suspension of sodium hydride (5.2 gms.; 0.11 mole) (50% suspension in mineral oil) in 100 ml of dry distilled DMF is added a solution of diethyl 1,4-dihydro-4-(2-trifluoromethylphenyl)-2,6-dimethyl-3,5-pyridine dicarboxylate (39.7 gms.; 0.1 mole) in 150 ml of DMF. After the gassing has ceased the reaction mixture is heated on a water bath for 1 hour and then is cooled to 50° C. and to the hot solution is added quickly a toluene solution of 2-chloro-N,N-dibenzyloxy-ethylethylamine. The reaction mixture is heated at 100°–110° C. for a period of 8 hours and then cooled. The unreacted NaH and NaCl is filtered off and then solvent removed from the filtrate. The residue is extracted with hot hexane which, on cooling, affords the product. Recrystallization from hexane followed by debenzylation using palladium on carbon yields pure desired product.

EXAMPLE V

Diethyl 1,4-dihydro-4-(2-nitrophenyl)-2,6-dimethyl-1-[2-(N-methyl-N-hydroxyethyl)aminoethyl]-3,5-pyridine dicarboxylate By substituting a solution of diethyl 1,4-dihydro-4-(2-nitrophenyl)-2,6-dimethyl-3,5-pyridine dicarboxylate for the 2-trifluoromethyl derivative and following the procedure of Example I, the pure product is obtained.

EXAMPLE VI

Diethyl 1,4-dihydro-4-(2-nitrophenyl)-2,6-dimethyl-1-[2-(N-hydroxyethyl-N-cyclohexyl)-aminoethyl]-3,5-pyridine dicarboxylate By substituting a solution of diethyl 1,4-dihydro-4-(2-nitrophenyl)-2,6-dimethyl-3,5-pyridine dicarboxylate for the 2-trifluoromethyl derivative and following the procedure of Example II, the pure product is obtained.

EXAMPLE VII

Diethyl 1,4-dihydro-4-(2-nitrophenyl)-2,6-dimethyl-1-[2-(N-hydroxyethyl)aminoethyl]-3,5-pyridine dicarboxylate By substituting a solution of diethyl 1,4-dihydro-4-(2-nitrophenyl)-2,6-dimethyl-3,5-pyridine dicarboxylate for the 2-trifluoromethyl derivative and following the procedure of Example III, the pure product is obtained.

EXAMPLE VIII

Diethyl 1,4-dihydro-4-(2-nitrophenyl)-2,6-dimethyl-1-[2-(N,N-dihydroxyethyl)aminoethyl]-3,5-pyridine dicarboxylate By substituting a solution of diethyl 1,4-dihydro-4-(2-nitrophenyl)-2,6-dimethyl-3,5-pyridine dicarboxylate for the 2-trifluoromethyl derivative and following the procedure of Example IV, the pure product is obtained.

What is claimed is:

1. A member selected from compounds of the formula

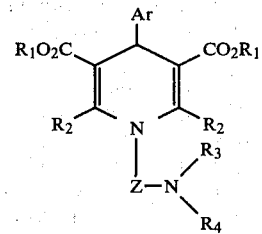

wherein Ar is thiophene, furan, pyridine, thiazole, pyrimidine, pyrrole, benzofuran, quinoline, benzothiophene, cycloalkyl having from 3 to 7 carbon atoms, naphthyl, indanyl, indenyl, tetrahydronaphthyl, or a radical of the formula

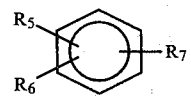

wherein each of $R_5$, $R_6$ and $R_7$ is independently H, alkyl, phenyl, halo, lower alkoxy, nitro, amino, alkylmercapto, cyano, carboxy, carbalkoxy, sulfamyl, trifluoromethyl, hydroxy, methanesulfonyl, or alkylamino; and $R_5$ and $R_6$ when taken together, form a methylenedioxy; Z is alkylene containing 1 to about 5 carbon atoms in the principal chain; each $R_1$ is independently hydrogen, alkyl or alkoxyalkyl, with the proviso that only one $R_1$ may be hydrogen; $R_2$ is lower alkyl; $R_3$ is hydroxyalkyl containing 2 to 4 carbon atoms and $R_4$ is H, alkyl, cycloalkyl or hydroxyalkyl containing 2 to 4 carbon atoms; wherein the alkyl and alkoxy groups contain up to 10 carbon atoms, and pharmaceutically-acceptable salts thereof.

2. The compound according to claim 1 wherein Ar is a monosubstituted phenyl group, Z is —CH$_2$—CH$_2$, $R_3$ is hydroxyethyl and $R_4$ is H, alkyl, cycloalkyl or hydroxyethyl.

3. A compound according to claim 1 wherein Ar is a trifluoromethylphenyl.

4. The compound according to claim 1 wherein Ar is a trifluoromethylphenyl, Z is —CH$_2$—CH$_2$—, $R_3$ is hydroxyethyl and $R_4$ is H, alkyl, cyclohexyl or hydroxyethyl.

5. A compound according to claim 1 wherein Ar is nitrophenyl.

6. A compound according to claim 1 wherein Ar is nitrophenyl, Z is —CH$_2$—CH$_2$—, $R_3$ is hydroxyethyl and $R_4$ is H, alkyl, cyclohexyl or hydroxyethyl.

7. Diethyl 1,4-dihydro-4-(2-trifluoromethylphenyl)-2,6-dimethyl-1-[2-(N,N-dihydroxyethyl)aminoethyl]-3,5-pyridine dicarboxylate.

8. A pharmaceutically-acceptable acid addition salt of the compound of claim 7.

9. Diethyl 1,4-dihydro-4-(2-nitrophenyl)-2,6-dimethyl-1-[2-(N-methyl-N-hydroxyethyl)aminoethyl]-3,5-pyridine dicarboxylate.

10. A pharmaceutically-acceptable acid addition salt of the compound of claim 9.

11. A member selected from antihypertensive compounds of the formula

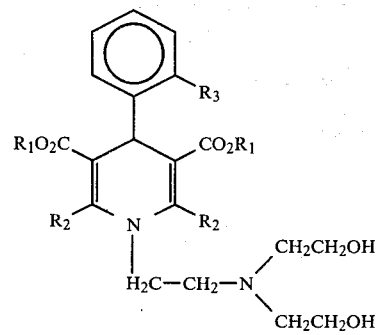

wherein $R_3$ is H, alkyl, phenyl, halo, lower alkoxy, nitro, amino, alkylmercapto, cyano, carboxy, carbalkoxy, sulfamyl, trifluoromethyl, hydroxy, methanesulfonyl, or alkylamino; and each $R_1$ and $R_2$ is lower alkyl; and acid addition salts thereof.

12. An anti-hypertensive compound according to claim 11 wherein $R_3$ is trifluoromethyl.

13. An anti-hypertensive compound according to claim 11 wherein $R_3$ is nitro.

14. A member selected from antihypertensive compounds of the formula

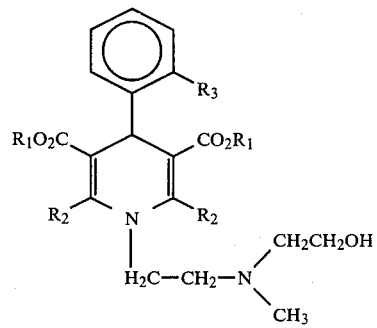

wherein $R_3$ is H, alkyl, phenyl, halo, lower alkoxy, nitro, amino, alkylmercapto, cyano, carboxy, carbalkoxy, sulfamyl, trifluoromethyl, hydroxy, methanesulfonyl, or alkylamino; and each $R_1$ and $R_2$ is lower alkyl; and acid addition salts thereof.

15. An anti-hypertensive compound according to claim 14 wherein $R_3$ is trifluoromethyl.

16. An anti-hypertensive compound according to claim 14 wherein $R_3$ is nitro.

* * * * *